(12) United States Patent
Gagne et al.

(10) Patent No.: US 10,126,278 B2
(45) Date of Patent: Nov. 13, 2018

(54) THERMAL STRESS RESISTANT MICRO-PLASMA EMISSION DETECTOR UNIT

(71) Applicant: LDETEK INC., Thetford Mines (CA)

(72) Inventors: Dany Gagne, Thetford Mines (CA);
Louis Paradis, Thetford Mines (CA);
Xavier Simard-Lecours, Levis (CA)

(73) Assignee: LDETEK INC., Thetford Mines, Quebec (CA)

( * ) Notice: Subject to any disclaimer, the term of this patent is extended or adjusted under 35 U.S.C. 154(b) by 0 days.

(21) Appl. No.: 15/446,781

(22) Filed: Mar. 1, 2017

(65) Prior Publication Data
US 2017/0254786 A1    Sep. 7, 2017

Related U.S. Application Data

(60) Provisional application No. 62/303,913, filed on Mar. 4, 2016.

(51) Int. Cl.
*G01J 3/28*     (2006.01)
*G01N 30/74*    (2006.01)
*G01N 21/67*    (2006.01)

(52) U.S. Cl.
CPC .............. *G01N 30/74* (2013.01); *G01N 21/67* (2013.01)

(58) Field of Classification Search
CPC ......... G01N 21/73; G01N 21/68; G01J 3/443; H01J 49/105; H05H 1/30
USPC ........................................................ 356/316
See application file for complete search history.

(56) References Cited

U.S. PATENT DOCUMENTS

| | | |
|---|---|---|
| 2,943,223 A | 6/1960 | Fay |
| 3,032,654 A | 5/1962 | Fay et al. |
| 3,549,326 A | 12/1970 | Dahlquist et al. |
| 4,167,334 A | 9/1979 | Phillips |
| 4,740,695 A | 4/1988 | Simpson |
| 4,806,315 A | 2/1989 | Daigle |
| 5,083,004 A | 1/1992 | Wells et al. |
| 5,153,519 A | 10/1992 | Wentworth et al. |
| 5,153,673 A | 10/1992 | Amirav |
| 5,218,203 A | 6/1993 | Eisele et al. |
| 5,394,092 A | 2/1995 | Wentworth et al. |
| 5,541,519 A | 7/1996 | Stearns et al. |
| 5,570,179 A | 10/1996 | Weckstrom |
| 5,594,346 A | 1/1997 | Stearns et al. |
| 5,611,846 A | 3/1997 | Overton et al. |
| 5,612,489 A | 3/1997 | Ragsdale et al. |
| 6,432,064 B1 | 8/2002 | Hibner et al. |

(Continued)

FOREIGN PATENT DOCUMENTS

GB    2344655 A    6/2000

*Primary Examiner* — Md M Rahman
(74) *Attorney, Agent, or Firm* — IPAXIO S.E.N.C.

(57) ABSTRACT

The micro-plasma emission detector unit is for use with a gas chromatograph. It includes an airtight housing having an internal ionization chamber, a pair of spaced-apart ionization electrodes positioned on opposite sides of the housing, and a set of opposite first and second holding members between which the housing is maintained inside the detector unit. Each electrode is maintained against an outer surface of the housing using a corresponding force-generating mechanism. With the proposed design, the risks of damaging the housing due to the thermal stresses are mitigated and the operating temperature of the detector unit can be increased.

20 Claims, 6 Drawing Sheets

(56) References Cited

U.S. PATENT DOCUMENTS

| | | |
|---|---|---|
| 6,490,910 B1 | 12/2002 | Butler et al. |
| 6,682,638 B1 | 1/2004 | Prohaska et al. |
| 6,691,552 B2 | 2/2004 | Cardelius |
| 7,013,707 B2 | 3/2006 | Prohaska et al. |
| 7,493,795 B2 | 2/2009 | Komura et al. |
| 7,586,092 B1 | 9/2009 | Karpetsky |
| 7,736,908 B2 | 6/2010 | Prohaska et al. |
| 7,812,614 B2 | 10/2010 | Kurita et al. |
| 7,824,471 B2 | 11/2010 | Gamache et al. |
| 7,902,498 B2 | 3/2011 | Miller et al. |
| 8,123,396 B1 | 2/2012 | Karpetsky et al. |
| 8,237,110 B2 | 8/2012 | Peng et al. |
| 8,239,171 B2 | 8/2012 | Gamache et al. |
| 9,310,308 B2 | 4/2016 | Paradis et al. |
| 2005/0230616 A1 | 10/2005 | Cameron et al. |
| 2006/0222938 A1* | 10/2006 | Yoshioka ............ H01M 2/0413 429/174 |
| 2007/0266858 A1* | 11/2007 | Alm ..................... G01N 30/463 96/105 |
| 2008/0231527 A1* | 9/2008 | Lemke ................... H01R 24/44 343/725 |
| 2008/0307888 A1* | 12/2008 | Yoshioka ............. B60Q 1/0023 73/627 |
| 2009/0031785 A1 | 2/2009 | Kellner et al. |
| 2010/0206454 A1* | 8/2010 | Maeda ............. H01L 21/67092 156/60 |
| 2012/0280061 A1* | 11/2012 | Pelagatti ................ G01N 30/12 239/290 |
| 2014/0160477 A1* | 6/2014 | Paradis .................. G01N 21/68 356/402 |
| 2014/0169144 A1* | 6/2014 | Briswalter ............. G04B 3/041 368/319 |
| 2014/0318711 A1* | 10/2014 | Wada ............... H01L 21/67092 156/378 |
| 2015/0244140 A1* | 8/2015 | Sukhman ............... H01S 3/038 372/36 |

* cited by examiner

THERMAL STRESS RESISTANT MICRO-PLASMA EMISSION DETECTOR UNIT

CROSS-REFERENCE TO RELATED APPLICATION

The present case claims the benefit of U.S. Patent Application No. 62/303,913 filed on 4 Mar. 2016, the content of which is hereby incorporated by reference in its entirety.

TECHNICAL FIELD

The technical field relates generally to micro-plasma emission detector units for use with gas chromatographs.

BACKGROUND

The basic chromatography is the separation of components of a sample owing to their differences in solubility or in adsorption in a stationary bed of a material (either liquid or solid). When the sample (moving phase) is a gas, the technique is referred to as gas-solid or gas-liquid chromatography, depending on whether the stationary phase is a solid or a liquid. In gas chromatography, a sample is introduced into a carrier gas as a vapor which flows through a chromatographic system. Upon separation by the stationary phase, the analytes travel through the gas chromatograph at different speeds and enter a detecting device, which device is connected to the gas chromatograph, at different times. As a result, individual analytes that are present in the sample may be identified by the detecting device.

The analytes are transported using a carrier gas. The carrier gas is an inert gas for the analyte. Argon, helium and nitrogen are examples of carrier gases. Other gases and mixtures of gases can be used as well, depending on the implementations and/or the requirements.

A same gas chromatograph can be used with different kinds of detecting devices, depending on the needs. The various kinds of detecting devices can themselves have different sensitivity levels. For instance, some detecting devices can be designed to detect very low concentrations of an analyte, such as in the range of parts per million (ppm). Others can be designed to detect concentrations in the range of a few percent or more.

Some detecting devices can measure the concentrations of analytes based on ionization. The carrier gas with the analytes is directed from the outlet of the gas chromatograph to an ionization chamber located in-between a pair of electrodes provided inside the detecting device. The detecting device is designed to transform the carrier gas and each analyte into plasma using the electrodes. The plasma results in light radiations, including visible light. The light radiations can be sensed and recorded using one or more corresponding light sensors. The spectral content of the data obtained from the light sensor or sensors can reveal the presence of some analytes and their concentration.

Temperature fluctuations inside a detecting device can result in undesirable variations of the photons emissions. It is thus generally desirable to keep the detecting device at a substantially constant temperature during the data collection and at a temperature that is minimally equal to the temperature of the incoming gases. Incoming gases having a temperature lower than that inside the detecting device will be heated by the hotter inner surfaces of the detecting device and the impact of the temperature difference will be minimized. The temperature inside the detecting device can be maintained substantially constant using a heat source and a temperature monitoring system. However, incoming gases having a temperature higher than that of the detecting device will tend to increase the temperature inside the detecting device, thereby causing temperature variations during operation that are often difficult to control. For at least this reason, keeping the temperature inside a detecting device higher than the incoming gases is generally desirable.

Operating a detecting device at a relative high temperature can also mitigate carbon deposits on the inner surfaces of the ionization chamber. There are generally less carbon deposits when the operating temperature is increased and this can prolong the lifespan of the detecting device.

While operating a detecting device at a relatively high temperature can be a desirable goal, the added mechanical stresses imposed on the detecting device create additional challenges. These added mechanical stresses include thermal stresses caused by the thermal expansion of the various parts inside the detecting device when heated from the room (ambient) temperature to its operating temperature. The temperature variations will change the size of the parts, either when their temperature increases or decreases. In this context, the expression "thermal expansion" also refers to material shrinkage, for instance when the parts cool back to the room temperature once the detecting device is switched off.

A detecting device based on a Dielectric Barrier Discharge (DBD) configuration can include an air-tight housing made of a material such as quartz or the like. The electrodes provided around the ionization chamber to create the plasma discharge therein must be constantly maintained in position and the usual approach to achieve this goal is to add an adhesive, such as epoxy, between each electrode and the corresponding surface on the housing. A material such as quartz is relatively fragile and prone to cracking. In general, a housing made of quartz can tolerate the thermal expansion of the electrodes if the operating temperature is relatively low, for instance up to 70 degrees C., but often not at a relatively high operating temperature, for instance 300 degrees C., where the risks of damaging the housing are very high. A temperature such as 200 degrees C. is still a relatively high operating temperature in this context.

Another challenge is maintaining the integrity of the gas circuit inside the detecting device. Air leaks into the gas circuit can contaminate the gas samples being analyzed and affect the results of the measurements. The various connections are thus designed in effort that they will remain air tight and that their integrity will be preserved regardless of the temperature. Adhesives such as epoxy have been used in the past to seal the junctions going in and out of a detecting device.

However, when these adhesives are subjected to relatively high temperatures, they can release chemical compounds in the gas circuit and thereby contaminate the gas samples. The ionization chamber will then no longer be a highly pure environment.

Accordingly, there is still room for many improvements in this area of technology.

SUMMARY

In one aspect, there is provided a micro-plasma emission detector unit according to a micro-plasma emission detector unit for use with a gas chromatograph, the detector unit including: an airtight housing having an internal ionization chamber, the housing including a carrier gas inlet and a gas outlet that are in fluid communication with the ionization chamber through internal passageways; a pair of spaced-apart ionization electrodes positioned on opposite sides of the housing, each electrode being maintained against an outer surface of the housing using a corresponding force-generating mechanism; and a set of opposite first and second holding members between which the housing is maintained inside the detector unit.

In another aspect, there is provided a micro-plasma emission detector unit as described and/or shown and/or suggested herein.

In another aspect, there is provided a method of configuring and/or operating a micro-plasma emission detector unit, as described and/or shown and/or suggested herein.

Details on the various aspects of the proposed concept will be apparent from the following detailed description and the appended figures.

DETAILED DESCRIPTION

Figure 1:
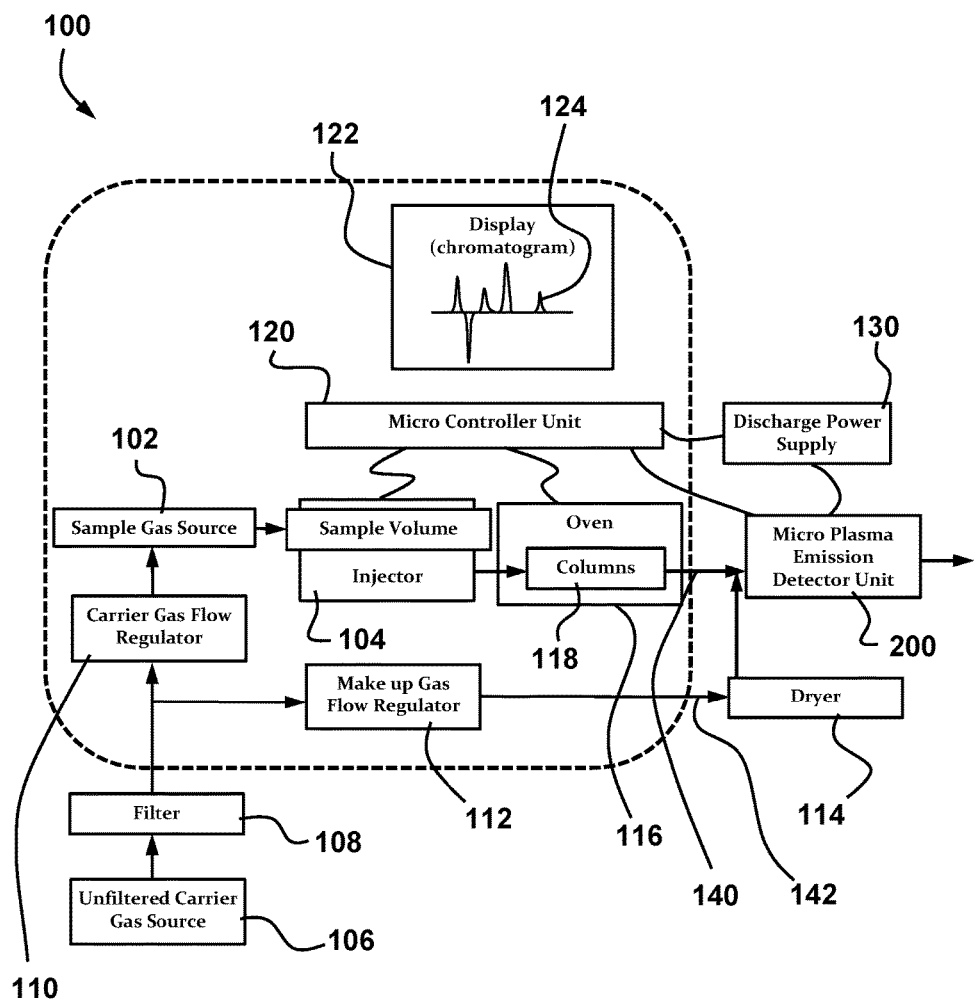
FIG. 1 is a schematic view illustrating a generic example of a gas chromatograph that can be used with a micro-plasma emission detector unit incorporating the proposed concept.

FIG. 1 is a schematic view illustrating a generic example of a gas chromatograph 100 that can be used with a micro-plasma emission detector unit 200 incorporating the proposed concept. This is only a simplified example and other kinds of gas chromatographs, configurations and arrangements are possible as well.

In the illustrated example, the gas chromatograph 100 receives a gas sample from a sample gas source 102. The gas sample coming from the sample gas source 102 is injected at an injector 104. The gas sample contains one or more analytes. Each analyte is a chemical compound to be analyzed.

Various parts inside and outside of the gas chromatograph 100 are in fluid communication with one another using a network of conduits and/or passageways. An example of such network is schematically illustrated in FIG. 1. Variants are possible as well.

In the illustrated example, the gas chromatograph 100 receives a carrier gas from an unfiltered carrier gas source 106, for instance one or more pressurized gas bottles. The analyte or analytes will be transported using the carrier gas. The carrier gas is an inert gas for the analyte or analytes.

Argon, helium and nitrogen are examples of carrier gases. Other gases and mixtures of gases can be used as well, depending on the implementations and/or the requirements.

In the illustrated example, the carrier gas coming from the carrier gas source 106 is filtered using a filter 108. The exact nature and construction of the filter 108 can vary from one implementation to another. It can also depend on the quality of the carrier gas from the carrier gas source 106. The filter 108 ensures that the carrier gas stream is substantially free of contaminants. This promotes the stability of the readings and the sensitivity of detection. The carrier gas is sent from the filter 108 to a carrier gas flow regulator 110. A portion of the carrier gas will also be used as makeup gas in this example. Variants as possible as well.

Furthermore, in the illustrated example, the makeup gas goes through a makeup gas flow regulator 112 and then through a dryer 114. The dryer 114 removes substantially all the water vapor present in the makeup gas, if any. The dryer 114 can be a part of the gas chromatograph 100 or be a separate device attached to it. The dryer 114 can be operated at room temperature and/or be heated using a heat source. It can include, for instance, dehydrated zeolite or a Zr-Vn-Fe alloy to capture any trace of residual OH doping agents. Variants are also possible as well. The dryer 114 can also be omitted in some implementations or be located elsewhere. Furthermore, some implementations may include a device to add a specific amount of OH doping agents to the makeup gas stream coming out of the dryer 114.

The gas sample, once injected in the carrier gas at the injector 104, is sent to an oven 116 having one or more gas separation columns 118. Each analyte will leave the column or columns 118, thus the gas chromatograph 100, at different times. The micro-plasma emission detector unit 200 is provided to measure the presence of one or more analytes and their concentration in the carrier gas stream at the outlet of the gas chromatograph 100. The detector unit 200 is located directly on the side of the gas chromatograph 100 in the illustrated example. Other arrangements and configurations are also possible, including having the detector unit 200 inside the gas chromatograph 100 in some implementations.

The carrier gas outlet of the gas chromatograph 100 is depicted in FIG. 1 at 140. The makeup gas outlet of the gas chromatograph 100 is depicted in FIG. 1 at 142. In the illustrated example, the carrier gas stream with the analyte or analytes to measure and the makeup gas stream coming from the dryer 114 are mixed together before entering the detector unit 200. This can be achieved, for instance, using a Y-shaped connector or another arrangement. It is also possible to mix the gases elsewhere in some implementations, for instance inside the detector unit 200 or even inside the gas chromatograph 100.

The mixed gas stream containing the makeup gas and the carrier gas with the analyte or analytes is sent to an ionization chamber located within the detector unit 200. The detector unit 200 receives each analyte from the gas chromatograph 100 at different times, for instance over the course of a few minutes from the time the gas sample was injected at the injector 104 until its entire content went through the column or columns 118 and out of the gas chromatograph 100. The detector unit 200 is designed to transform the mixed gas and each analyte therein into plasma using a pair of opposite electrodes provided around the ionization chamber. The plasma results in light radiations, including visible light. The light radiation resulting from the plasma will vary from one analyte to another, thus over the given time period. The spectral content will reveal the presence of a given analyte and its concentration. Data regarding the light radiations will be recorded throughout this process.

In the illustrated example, the gas chromatograph 100 of FIG. 1 includes a micro-controller unit 120 for controlling the different parts, for instance the carrier gas flow regulator 110, the makeup gas flow regulator 112, the oven 116, various valves that can be provided on the network of conduits and/or passageways, and the detector unit 200. The micro-controller unit 120 can also record data coming from the detector unit 200. Other configurations and arrangements are possible as well.

Also in the illustrated example, data signals from the detector unit 200 can be in the form of analog signals and these signals can be converted to digital signals by the micro-controller unit 120 before being transferred to another device, for instance a computer system or the like. The micro-controller unit 120 can also analyze data signals and display chromatograms, for instance using a computer screen 122 as depicted in FIG. 1. A schematic and generic example of a chromatogram 124 is shown. A chromatogram is a visual representation of the spectral content of the light radiation received from the plasma over the time period. Variants are possible as well.

FIG. 1 shows that the detector unit 200 of the illustrated example is connected to a discharge power supply 130. The discharge power supply 130 is designed to provide AC or DC voltage at given frequencies, for instance between 60 Hz and 100 kHz, to the electrodes inside the detector unit 200. This discharge power supply 130 can be controlled using the micro-controller unit 120, as shown. For instance, the micro-controller unit 120 can provide a DC voltage between more than 0 to 12 V DC at the primary side of the discharge power supply 130. Other values are also possible. The secondary side of the discharge power supply 130 will then provide the higher voltage to the electrodes so as to create the plasma discharges inside the ionization chamber of the detector unit 200. The discharge power supply 130 is connected to the detector unit 200 using corresponding electric cables or the like. The exact construction, configuration and operational parameters of the discharge power supply 130 can vary from one implementation to another.

Figure 2:
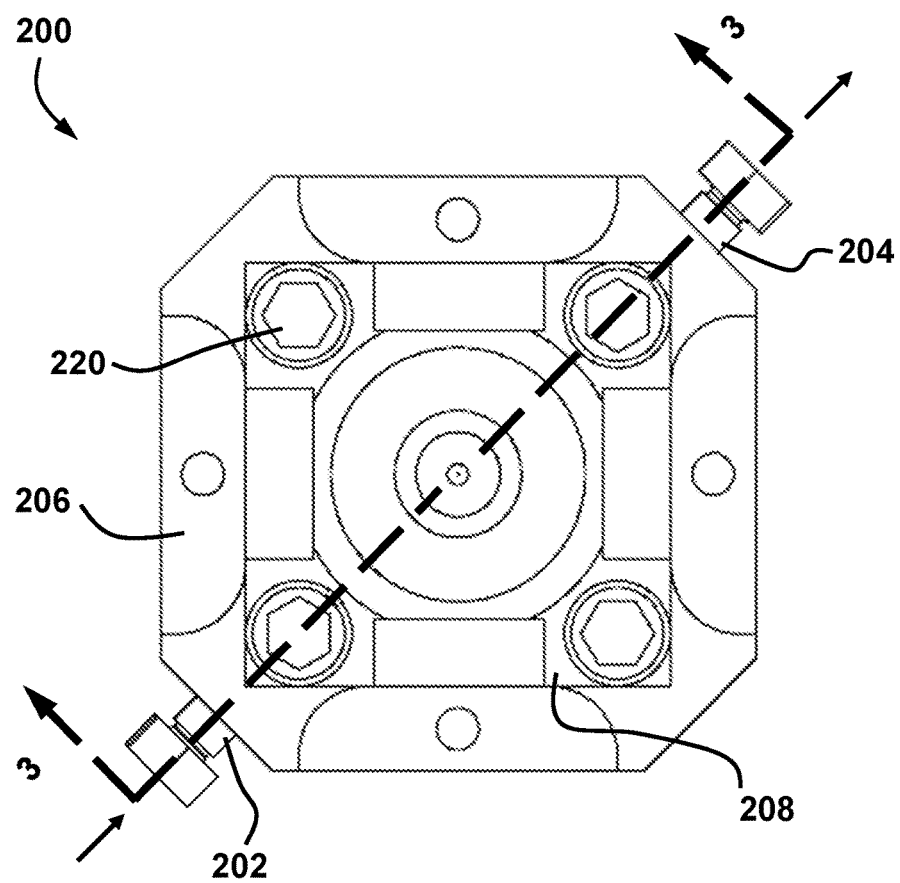
FIG. 2 is a top plan view illustrating an example of a micro-plasma emission detector unit incorporating the proposed concept.

FIG. 2 is a top plan view illustrating an example of a micro-plasma emission detector unit 200 incorporating the proposed concept. Variants of the illustrated example are possible as well. As can be seen, the mixed gas stream enters the detector unit 200 at a gas inlet 202. The gas inlet 202 includes a fitting with a threaded portion secured to a corresponding threaded socket that is provided on the side of a first holding member 206. This first holding member 206 forms the bottom base of the detector unit 200 in the example. The detector unit 200 includes a mixed gas circuit extending therein from the gas inlet 202 to a gas outlet 204. This gas circuit passes through an ionization chamber provided inside the detector unit 200. The gases exit the detector unit 200 through the gas outlet 204 before being discarded. The gas outlet 204 of the illustrated example also includes a fitting with a threaded portion secured to a corresponding threaded socket that is provided on the side of the first holding member 206. Variants are possible as well.

The detector unit 200 further includes a second holding member 208. This second holding member 208 is a distinct part and forms the top section of the detector unit 200 in the illustrated example.

Figure 3:
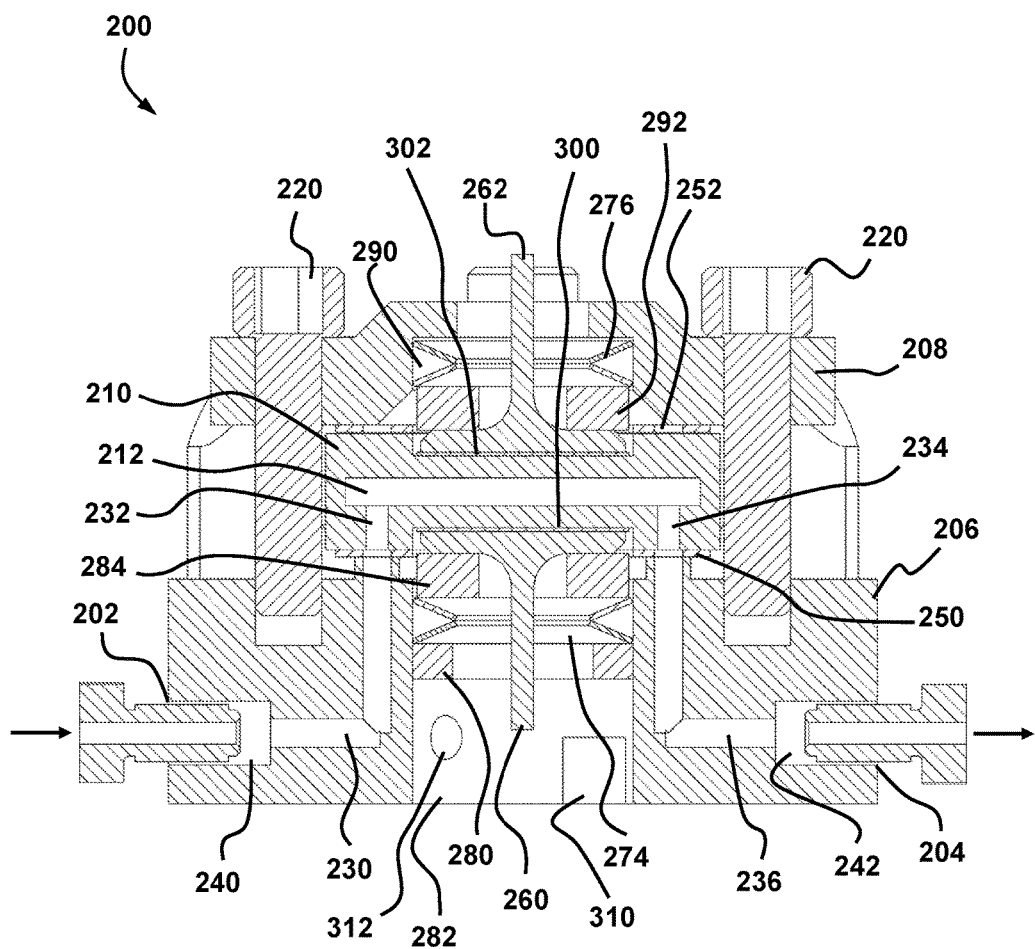
FIG. 3 is a cross-sectional view taken along line 3-3 in FIG. 2.

FIG. 3 is a cross-sectional view taken along line 3-3 in FIG. 2. As can be seen, the detector unit 200 includes a housing 210 in which is located an ionization chamber 212. The housing 210 is held in position between opposite first and second holding members 206, 208. These two members 206, 208 are attached together using removable fasteners, more particularly a set of four symmetrically-disposed bolts 220 in the example. Variants are possible as well. For instance, the number of bolts 220 can be different or other kinds of connectors can be used.

The first holding member 206 shown in FIG. 3 includes a first internal passageway 230 machined in the housing 210 to allow the mixed gas entering the detector unit 200 through the gas inlet 202 to flow to the ionization chamber 212. This passageway 230 is formed by two juxtaposed and perpendicularly-disposed channels in the illustrated example, for instance made by drilling narrow holes. The passageway 230 preferably has a circular cross section with a diameter between 0.5 mm and 5 mm, more preferably between 2 mm and 3 mm. These dimensions are generally optimum for many implementations. Variants are possible as well.

From the outlet end of the passageway 230 of FIG. 3, the gas circuit enters the housing 210 through a first passageway 232 made through a wall of the housing 210. This first housing passageway 232 can also have a circular cross section and is in registry with the outlet end of the first passageway 230. The first housing passageway 232 ends inside the ionization chamber 212. The housing 210 also includes a second passageway 234 located at an opposite side of the ionization chamber 212.

The two passageways 232, 234 are disposed so to promote a good air flow within the ionization chamber 212 during operation. From the second housing passageway 234, the gas circuit of FIG. 3 continues into a second passageway 236 made into the first holding member 206 and that is in registry with the second housing passageway 234. This second passageway 236 is also formed by two juxtaposed and perpendicularly-disposed channels in the illustrated example. The outlet end of the second passageway 236 corresponds to the gas outlet 204 of the detector unit 200. Variants are possible as well.

FIG. 3 further shows the two threaded sockets 240, 242 in which the fitting of the gas inlet 202 and the fitting of the gas outlet 204 of the illustrated example are attached, respectively. Variants are possible as well. The first and second holding members 206, 208, as well as the bolts 220, are preferably made of the same material. This way, the thermal expansion coefficient will be the same everywhere. Nevertheless, variants are possible as well. The material for these parts is preferably a metal or an alloy having a relatively low thermal expansion coefficient. One possible example is tungsten, where the linear thermal expansion coefficient is about 2.5 micro inch/degree F. Other materials are possible, including stainless steel since its linear thermal expansion coefficient is generally below 6 micro inch/degree F. Having a minimal surface adsorption and a maximal inertness to alleviate chemical reactions with the gases sent through the gas circuit are also highly desirable characteristics. However, the internal surface that will be in contact with the mixed gases can be coated with a layer of another material so as to improve the surface inertness.

The housing 210 has a substantially rectangular outer shape in the illustrated example but variants are possible. For instance, the housing 210 can have a triangular or hexagonal shape, to name just a few. Many other variants are possible.

The housing 210 of the illustrated example is provided as a monolithic block of a material, namely a component where all sides are fused into a single solid and seamless piece. This way, the housing 210 will remain air tight at all times despite the thermal expansion. The material for the housing 210 is also a dielectric material that allows maximum inertness with the analyte or analytes, and a material that is considered as being transparent, particularly to ultraviolet (UV) light radiations, across a thin layer of this material. Examples of possible materials include crystal quartz, fused silica, borosilicate, industrial grade sapphire, synthetic diamond and glass. These materials allow good light transmission from UV to infrared spectrum, have a good compression resistance and inertness, and a relatively low thermal expansion coefficient. Nevertheless, other materials are possible as well.

In the illustrated example, the material is a highly-purified synthetic quartz. This material can have a response of about 80% in the spectral range between 180 and 2900 nm. Melted natural crystalline quartz offers a response of about 80% in the spectral range between 230 and 3500 nm and thus, can also be used as a material for the housing 210. These materials offer a relatively large spectral response and are fusible. Nevertheless, variants are possible as well.

The housing 210 can be made of two distinct synthetic quartz workpieces machined separately using high precision manufacturing techniques since they are generally relatively small in size. The two workpieces are then fused together at a high temperature to ensure a permanent and perfect interconnection between their corresponding mating faces. Once fused, the two workpieces form a monolithic block. The housing 210 can be made very small, for instance having a few millimeters in size. Variants are possible.

In the illustrated example, a first gasket 250 is provided between the first holding member 206 and the bottom outer surface of the housing 210. This gasket 250 can be annular and will act as a cushion between the two parts. It also includes two apertures that are in registry with the junctions between the corresponding pairs of passageways 230, 232 and 234, 236. The gasket 250 will compensate for the thermal expansion of parts and seals the junctions where the gas circuit passes. The thickness of the gasket 250 is preferably from 25 micron to 200 microns, more preferably from 100 to 125 microns. These values generally offer good sealing properties and are enough to create a smooth junction that can mitigate the mechanical stresses on the housing 210 due the thermal expansion of the parts. The holding pressures from the assembly is also more smoothly applied on the housing 210. Variants are possible as well.

A gasket 252 is also provided between the top surface of the housing 210 and the bottom of the second holding member 208. This second gasket 252 is essentially used as a cushion. If desired, one can used the exact same gasket model and size for the two gaskets 250, 252 for the sake of simplicity. They can also be different models. Still, the gaskets 250, 252 can be made of a material such as Polyimide, Kapton™, Teflon™, Buna™, polytetrafluoroethylene (PTFE) or others. The gaskets 250, 252 of the illustrated example are preferably made of a layer polyimide that is machined to create the holes. Nevertheless, variants are possible as well, including not using one or even both gaskets in some implementations.

As aforesaid, the bolts 220 are provided to hold the housing 210 between the two holding members 206, 208 of the illustrated detector unit 200. The distal end of the bolts 220 is secured into corresponding threaded bore holes made on the top face of the first holding member 206. The bolts 220 are tighten to maintain a constant minimal holding force on the housing 210 once positioned between the first and second holding members 206, 208. The holding force will prevent the parts from moving and will also contribute in creating a constant air-tight seal between passageways 230, 236 of the first holding member 206 and the corresponding passageways 232, 234 of the housing 210. This mitigates contamination risks and ensures a highly-pure environment inside the ionization chamber 212. The holding force can be adjusted by tightening or loosening the bolts 220. Variants are possible as well.

The assembly formed by the first holding member 206, the second holding member 208 and the housing 210 in-between can be covered by an external housing (not shown) to mitigate heat losses during operation and to conceal the hot surfaces.

FIG. 3 shows the two opposite electrodes 260, 262 that are located around the housing 210 of the detecting unit 200, more particularly against corresponding outer surfaces of the housing 210. They are positioned to be in registry with the ionization chamber 212. The electrodes 260, 262 are made of a material having good electrical conductivity characteristics to optimize the ionization discharge and to minimize the energy consumption. This material can be, for instance, nickel, brass or any other metal and/or alloy offering good electrical conductivity characteristics. Electrodes made of nickel are often preferred because of the good electrical conductivity of this material. Variants are possible as well.

In the illustrated example, the head of each electrode 260, 262 is positioned inside a corresponding cavity machined on the bottom and top outer surfaces of the illustrated housing 210, respectively. The proximal surface of each electrode head is flat. The width of the cavities is made slightly larger than that of the heads of these electrodes 260, 262. The free space around the electrode heads will provide room for the thermal expansion and mitigate the mechanical stresses on the housing 210. The heads of the electrodes 260, 262 can also be positioned differently, for instance simply against corresponding flat surfaces, in other implementations. Other variants are possible as well.

The detector unit 200 uses instead a pair of force-generating mechanisms 270, 272 to maintain the corresponding electrodes 260, 262 firmly in position against the outer wall surfaces of the housing 210. Among other things, the force-generating mechanisms 270, 272 alleviate the need for the electrodes 260, 262 to be bonded to the housing 210 using an adhesive, for instance epoxy. The electrodes 260, 262 are also not engaged directly by the holding members 206, 208. Hence, the materials used for making the electrodes 260, 262 can now be chosen based almost exclusively on the electrical conductivity characteristics and the thermal expansion coefficient of the electrodes 260, 262 is no longer a concern.

In the example illustrated in FIG. 3, the force-generating mechanisms 270, 272 each include a compression spring 274, 276, respectively. In the force-generating mechanism 270 located at the bottom, the bottom end of the compression spring 274 rests against the top annual face of a ring-shaped support 280. The outer side of the ring-shaped support 280 includes outer threads engaging corresponding inner threads provided on the wall of a large central cylindrical cavity 282 located inside the first holding member 206. This central cavity 282 is made just large enough to pass the head of the bottom electrode 260 therein. The shank of the bottom electrode 260 extends downwardly at the center of the cavity 282 once the electrode 260 is in position. The top end of the compression spring 274 rests against the bottom annular surface of a ring-shaped dielectric spacer 284. This dielectric spacer 284 insulates the bottom electrode 260 from the surrounding metallic parts. It engages the back side of the head of the electrode 260. The force exerted by the compression spring 274 keeps the front side of the head of the bottom electrode 260 firmly against the corresponding wall surface on the housing 210 and secure it into position. The force can be adjusted for instance by changing the spring 274 and/or by changing the position of the ring-shaped support 280 with reference to the head of the electrode 260. Variants are possible as well.

Furthermore, in the force-generating mechanism 272 located at the top in the example illustrated in FIG. 3, the bottom side of the compression spring 276 rests against an inner surface of a cavity 290 inside the second holding member 208. The shank of the top electrode 262 extends upwardly and through a central hole on the second holding member 208. The bottom side of the compression spring 276 rests against the top annular surface of a ring-shaped dielectric spacer 292. The dielectric spacer 292 insulates the top electrode 262 from the surrounding metallic parts. It engages the head of the electrode 262. The force exerted by the compression spring 276 keeps the front side of the head of the top electrode 262 firmly against the corresponding surface on the housing 210 and secure it into position. The force can be adjusted by changing the spring 276, for instance. Variants are possible as well.

The positive forces applied on the electrodes 260, 262 by the force-generating mechanisms 270, 272 ensure a good electrical conductive contact between the surfaces. Replacing the electrodes 260, 262 is now also very easy since they are not held by adhesives. The electrodes 260, 262 can be easily and quickly replaced, for instance in the context of a maintenance operation or for reconfiguring the detector unit 200.

Figure 4:
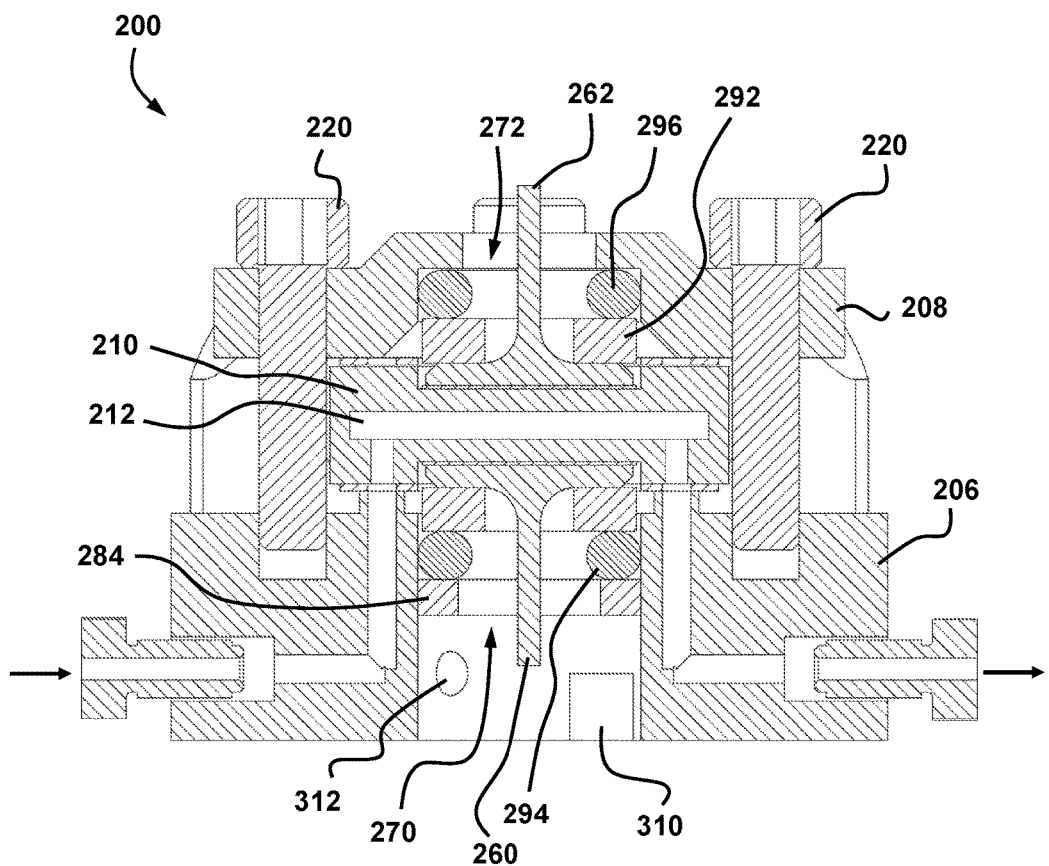
FIG. 4 is a view similar to FIG. 3 but illustrating a variant thereof.

FIG. 4 is a view similar to FIG. 3 but it illustrates a variant of the detector unit 200, more particularly a variant of the force-generating mechanisms 270, 272. In this example, the force-generating mechanisms 270, 272 include toric-shaped elements 294, 296 instead of springs to store mechanical energy between each electrode 260, 262 and the corresponding wall surface on the housing 210. The elements 294, 296 can be made of a material such as a perfluoroelastomer, for instance one sold under the trademark Kalrez®. Other kinds of materials and other configurations of force-generating mechanisms can also be used. The other parts of the detector unit 200 in the example shown in FIG. 4 are the same or similar as the ones in the example shown in FIG. 3.

The examples illustrated in FIGS. 3 and 4 also include cushions 300, 302 provided between the corresponding electrodes 260, 262 and the housing 210 to temper the contact engagement. These cushions 300, 302 preferably have a thickness between 25 micron and 50 microns. These dimensions are generally optimum for many implementations. They are made of a dielectric material, such as polyimide, Kapton™, Teflon™, Buna™, PTFE or others. Nevertheless, one can omit one or even both cushions 300, 302 in some implementations.

The ionization chamber 212 preferably has an internal air gap (height) between 0.5 mm to 5 mm, more preferably between 1 mm to 3 mm. These dimensions are generally optimum for many implementations. Likewise, the thickness of the walls between each electrode 260, 262 and the interior of the ionization chamber 212 is preferably between 0.5 mm and 4 mm, more preferably between 1 mm and 3 mm. The size of the ionization chamber 212 is preferably between 2 mm by 2 mm and 30 mm by 30 mm, preferably 10 mm by 10 mm. Other shapes and/or dimensions are possible as well.

If desired, one can provide a slightly-raised shoulder surface around the periphery of the hole where the passageways of the first holding member 206 are located. These raised surfaces can be machined by removing material everywhere else on the corresponding top surface of the first holding member 206 to enhance the sealing between the parts. This sealing technique reduces the force required on the gasket 250 to seal the passageways by offering a sealing at a precise junction. It can extend the lifespan of the gasket 250 and minimize the risks of cracking due to the reduced force that is necessary to obtain the sealing. With this arrangement, using adhesives such as epoxy at the junctions can be omitted.

The detector unit 200 can be heated with the heater assembly 310. This heater assembly 310 can be mounted on the first holding member 206, for instance in or near the central cavity 282 as shown in the illustrated example. It is thus not directly provided on the housing 210 and, as a result, heat will be more evenly distributed on the housing 210. A resistance temperature device (RTD) 312 can be provided to monitor the temperature inside the detector unit 200 and thereby allow a precise control of the temperature. The heater assembly 310 can have different forms, for instance be provided as a removable cartridge or be in the form of a layer attached to a surface. The heater assembly 310 can also be provided on the second holding member 208. Other variants are possible as well.

Figure 5:
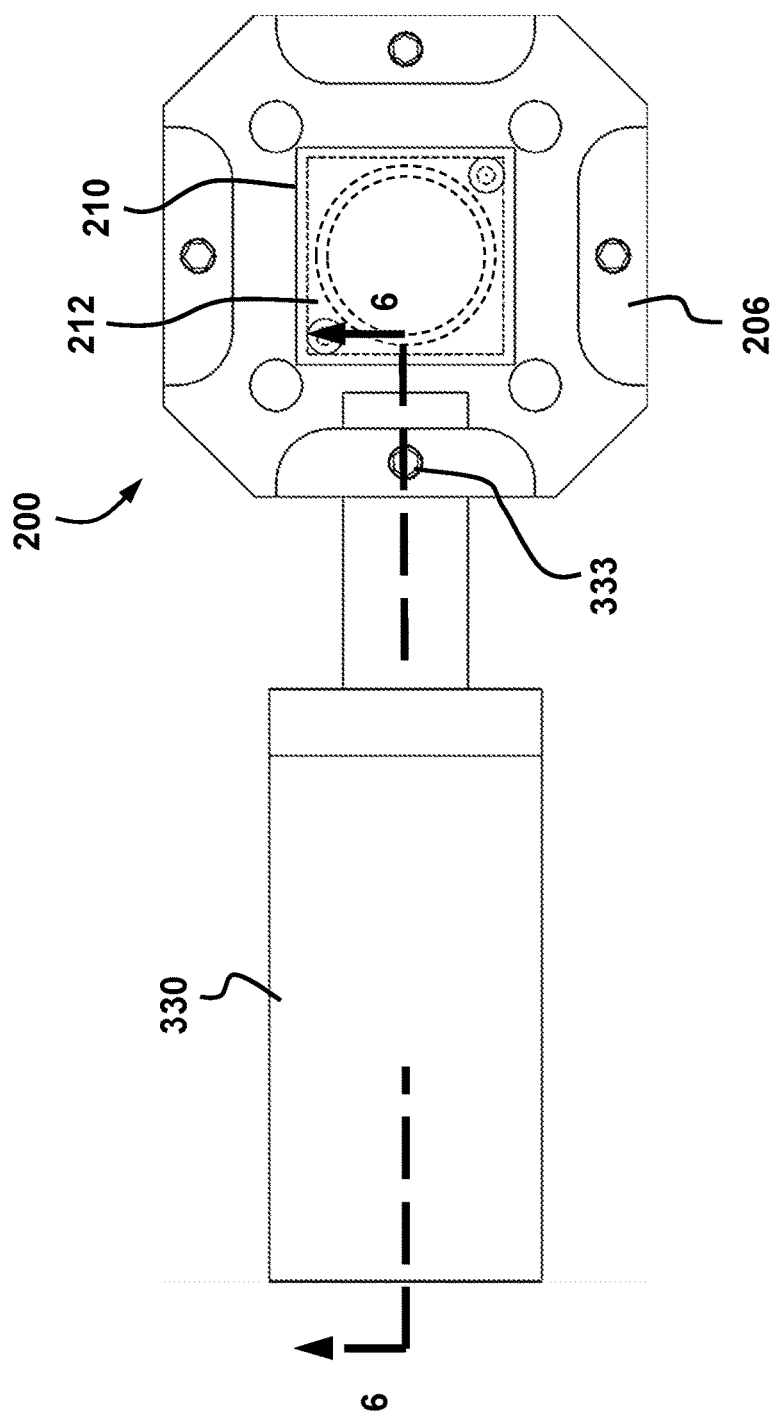
FIG. 5 is a top plan view of the detector unit of FIG. 2 that includes an example of a light collector.
Figure 6:
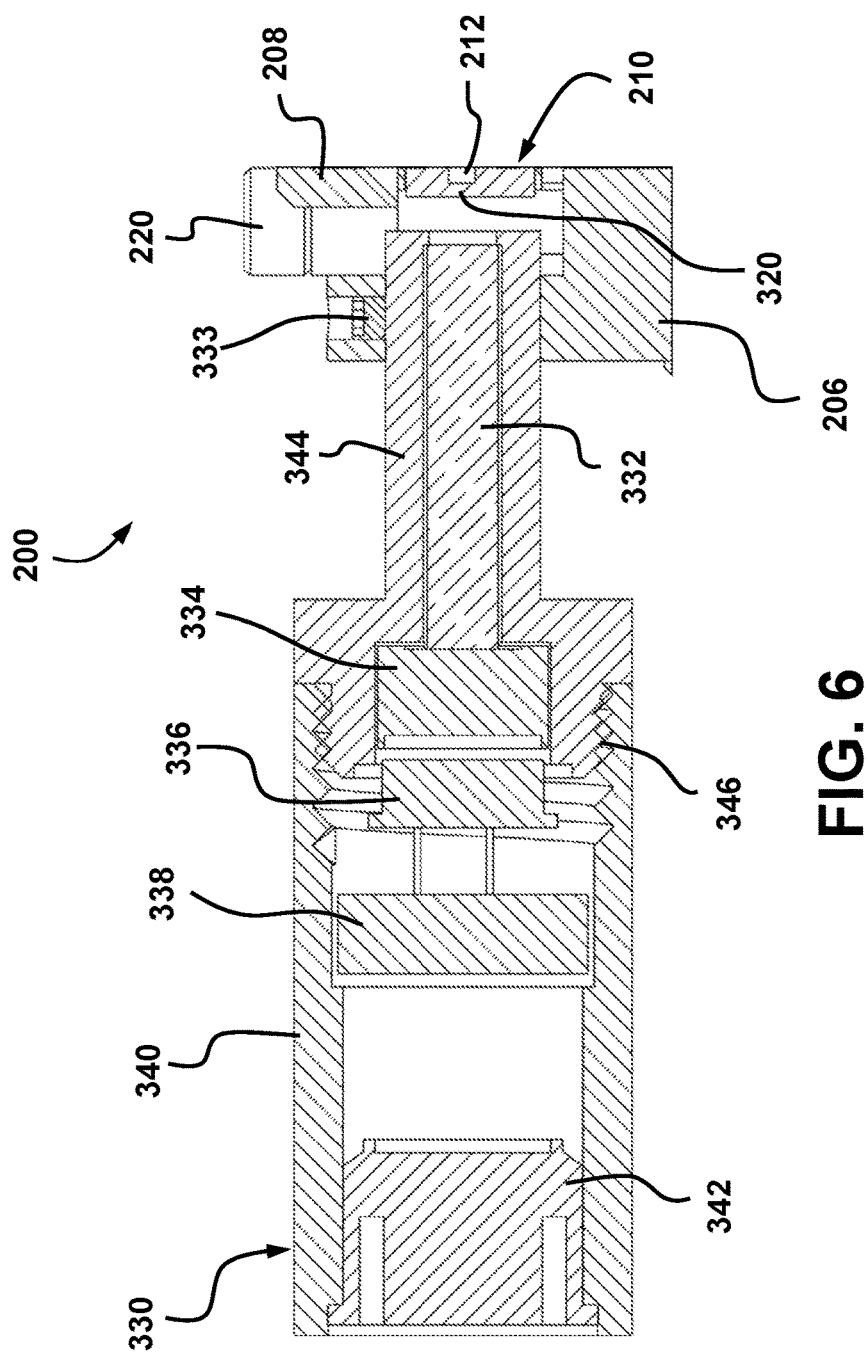
FIG. 6 is a cross-sectional view taken along line 6-6 in FIG. 5.

FIG. 5 is a top plan view of the detector unit 200 of FIG. 2 that includes an example of a light collector 330. Only one of the light collectors 330 of the detector unit 200 is shown for the sake of simplicity. FIG. 6 is a cross-sectional view taken along line 6-6 in FIG. 5.

Each lateral side surface of the housing 210 includes a light collection window 320 (FIG. 6) that is adjacent to the ionization chamber 212. The rectangular-shaped housing 210 of the illustrated detector unit 200 includes four light collection windows 320. These light collection windows 320 are directly integrated into the housing 210 in the illustrated example in the form of a thinner wall portion. Thus, no additional parts are required. This design is highly desirable since, as aforesaid, it greatly simplifies the airtightness of the housing 210. Nevertheless, variants are possible. For instance, one can also use more or less than four light collection windows 320, depending on the needs and the shape of the housing 210. Other variants as possible as well.

The thin wall at each light collection window 320 is machined so as to be substantially free of imperfections and with a high degree of flatness, for instance being less than 0.002 mm (2 μm), to optimize the light transmission. The light collection windows 320 of the illustrated example are also substantially perfectly flat surfaces to alleviate light reflection and/or diffusion. Imperfections could otherwise result in a loss in the amount of light radiations being transmitted through the wall of a given light collection window 320 and this can decrease the sensitivity of the detector unit 200 for one or more analytes.

Photons coming out of the housing 210 through the light collection windows 320 are collected by the light collectors 330. In the example illustrated in FIGS. 5 and 6, the light guide 332 inside the light collector 330 is basically in the form of a cartridge having a diameter between 1 mm and 10 mm. These dimensions are generally optimum to collect light coming out of the ionization chamber 212. The tip of the light collector 330 is aligned with the corresponding light collection window 320 and in the illustrated example, it is maintained in position using a corresponding set screw 333. Variants are possible. The light collection can also be done using an optic fiber, a mirror or other light collection devices.

A proper alignment of the light collector 330 ensures that there is no loss of signal. The set screw 333 used in the illustrated example also allow adjusting the position of the tip of the light collector 330 from the outer surface of the light collection window 320, for instance at a distance between 0.5 mm to 3 mm. The spacing at the tip maintains a good signal response and the light collector 330 is prevented from touching the housing 210 so to mitigate the risks of breaking the housing 210. Each set screw 333 is set inside a corresponding threaded hole located on the first holding member 206. The light collector 330 is inserted through an opening on the side of the first holding member 206. Variants are possible as well.

In the illustrated example, the light entering the light guide 332 inside the light collector 330 goes to an optical filter 334 and then to a photodiode 336. This photodiode 336 has an amplifier printed circuit board 338. These parts are mounted inside a cylindrical casing 340. A connector port 342 is provided at the end and signals can be sent to another device, for instance to the micro controller unit 120 (FIG. 1), through this connection. The data processing can be done at the micro controller unit 120 or using another device or system. Variants are possible as well.

The casing 340 can be made of a material such as a stainless steel alloy, brass, nickel or aluminum, to name just a few examples. Stainless steel is generally preferred. The casing 340 is generally located at a distance between 10 mm to 50 mm from the housing 210. This distance mitigates the heat transfer to the parts inside the casing 340, particularly when the detector unit 200 is operated at a relatively high temperature. In the illustrated example, a thermally insulated fitting 344 is located at the tip of the light collector 330. This fitting 344 is set around the light guide 332 and is preferably made of a material that offers good thermal insulation characteristics, such as Teflon™, polyoxymethylene (Derlin™) or borosilicate, to name just a few examples. Polyoxymethylene is generally preferred. The fitting 344 is attached to the casing 340 in a way that can keep the heat transfer to a minimum. In the illustrated example, an internal screw arrangement 346 secures the fitting 344 to the casing 340. Variants are possible as well.

The configuration of the light collectors 330 allows them to be easily positioned and replaced, for instance for maintenance or for a reconfiguration. It is thus possible for an end user to have different kinds of interchangeable light collectors 330, depending on the desired light spectrum of interest for a specific application.

Overall, with the proposed design, the risks of damaging the housing 210 due to the thermal stresses are mitigated and, if desired, the operating temperature of the detector unit 200 can be significantly increased compared to current operating temperature. The integrity of the gas circuit inside the detector unit 200 is also preserved at all temperatures when using the proposed approach.

The present detailed description and the appended figures are meant to be exemplary only. A skilled person will recognize that variants can be made in light of a review of the present disclosure without departing from the proposed concept.

LIST OF REFERENCE NUMERALS 100 gas chromatograph
102 sample gas source
104 injector
106 carrier gas source
108 filter
110 carrier gas flow regulator
112 makeup gas flow regulator
114 dryer
116 oven
118 column
120 micro-controller unit
122 computer screen
124 chromatogram
130 discharge power supply
140 carrier gas outlet
142 makeup gas outlet
200 detector unit
202 gas inlet
204 gas outlet
206 first holding member
208 second holding member
210 housing
212 ionization chamber
220 bolt
230 first passageway (first holding member)
232 first housing passageway
234 second housing passageway
236 second passageway (first holding member)
240 socket
242 socket
250 bottom gasket
252 top gasket
260 bottom electrode
262 top electrode
270 bottom force-generating mechanism
272 top force-generating mechanism
274 bottom spring
276 top spring
280 ring-shaped threaded support
282 central cavity (first holding member)
284 bottom ring-shaped dielectric spacer
290 cavity (second holding member)
292 top ring-shaped dielectric spacer
294 bottom toric-shaped element
296 top toric-shaped element
300 cushion (for bottom electrode)
302 cushion (for top electrode)
310 heater assembly
312 resistance temperature device (RTD)
320 light collection window
330 light collector
332 light guide
333 set screw
334 optical filter
336 photodiode
338 printed circuit board
340 casing
342 connector port
344 thermally insulated fitting
346 screw arrangement

What is claimed is:

1. A micro-plasma emission detector unit for use with a gas chromatograph, the detector unit including:
    an airtight housing having an internal ionization chamber, the housing including a carrier gas inlet and a gas outlet that are in fluid communication with the ionization chamber through internal passageways;
    a pair of spaced-apart ionization electrodes positioned on opposite sides of the housing;
    a pair of force-generating mechanisms, each electrode being maintained against an outer surface of the housing using a corresponding one of the force-generating mechanisms; and
    a set of opposite first and second holding members between which the housing is maintained inside the detector unit.

2. The detector unit as defined in claim 1, wherein the housing is made of a monolithic block of a transparent material.

3. The detector unit as defined in claim 2, wherein the housing is made of quartz.

4. The detector unit as defined in claim 1, wherein at least one of the force-generating mechanisms includes a compression spring.

5. The detector unit as defined in claim 4, further including a dielectric spacer positioned between at least one of the electrodes and a first end of the compression spring.

6. The detector unit as defined in claim 5, wherein the first and second holding members are attached together by a plurality of removable fasteners.

7. The detector unit as defined in claim 1, wherein at least one of the force-generating mechanisms includes a toric-shaped resilient element.

8. The detector unit as defined in claim 7, further including a dielectric spacer positioned between at least one of the electrodes and the toric-shaped resilient element.

9. The detector unit as defined in claim 8, wherein the first and second holding members are attached together by a plurality of removable fasteners.

10. The detector unit as defined in claim 1, wherein the first holding member includes passageways that are in registry with corresponding passageways made inside the housing and that lead in and out of the ionization chamber.

11. The detector unit as defined in claim 10, further including:
a first gasket between the housing and the first holding member, the first gasket including at least two holes around junctions between the passageways; and
a second gasket between the housing and the second holding member.

12. The detector unit as defined in claim 1, further including a cushion between a front side of a head of each electrode and a corresponding surface on the housing.

13. The detector unit as defined in claim 12, wherein the electrode heads are located inside respective cavities in the housing that are larger in width than the heads of the electrodes.

14. The detector unit as defined in claim 1, wherein the light collection is performed using at least one light collector positioned on a side of the housing.

15. The detector unit as defined in claim 14, wherein each light collector includes a thermally-insulated fitting in which a light guide is provided.

16. The detector unit as defined in claim 1, further including using raised circular areas that allow to increase the gasket deformation locally on sealing points.

17. A micro-plasma emission detector unit for use with a gas chromatograph, the detector unit including:
an airtight housing having an internal ionization chamber, the housing including a carrier gas inlet and a gas outlet that are in fluid communication with the ionization chamber through internal passageways;
a pair of spaced-apart ionization electrodes positioned on opposite sides of the housing, each electrode being maintained against an outer surface of the housing using a corresponding force-generating mechanism;
a set of opposite first and second holding members between which the housing is maintained inside the detector unit;
at least one of the force-generating mechanisms includes a compression spring; and
a dielectric spacer positioned between at least one of the electrodes and a first end of the compression spring, the compression spring having a second end, opposite to the first end, that engages a ring-shaped threaded support mounted inside a central cylindrical cavity provided in one of the holding members.

18. A micro-plasma emission detector unit for use with a gas chromatograph, the detector unit including:
an airtight housing having an internal ionization chamber, the housing including a carrier gas inlet and a gas outlet that are in fluid communication with the ionization chamber through internal passageways;
a pair of spaced-apart ionization electrodes positioned on opposite sides of the housing, each electrode being maintained against an outer surface of the housing using a corresponding force-generating mechanism;
a set of opposite first and second holding members between which the housing is maintained inside the detector unit;
at least one of the force-generating mechanisms includes a toric-shaped resilient element; and
a dielectric spacer positioned between at least one of the electrodes and the toric-shaped resilient element, the toric-shaped resilient element engaging a ring-shaped threaded support mounted inside a central cylindrical cavity provided in one of the holding members.

19. The detector unit as defined in claim 17, further including at least one heater assembly mounted inside the central cavity.

20. The detector unit as defined in claim 18, further including at least one heater assembly mounted inside the central cavity.

* * * * *